(12) United States Patent
Eggenreich et al.

(10) Patent No.: US 6,676,956 B1
(45) Date of Patent: Jan. 13, 2004

(54) OIL-IN-WATER EMULSION FOR PROTECTING HUMAN ORGANS AGAINST PEROXIDATION

(75) Inventors: Udo Eggenreich, Graz (AT); Norbert Feichtinger, Graz (AT); Gerald Hofer, Unterpremstätten (AT); Karin Schaupp, Graz (AT); Klaus Sommermeyer, Rosbach v.d.H. (DE); Anneliese Wurm, Graz (AT); Eckhard Nagel, Wedemark (DE); Andreas Meyer zu Vilsendorf, Bünde (DE)

(73) Assignee: Fresenius Kabi Austria GmbH (AT)

( * ) Notice: Subject to any disclaimer, the term of this patent is extended or adjusted under 35 U.S.C. 154(b) by 0 days.

(21) Appl. No.: 09/868,789

(22) PCT Filed: Dec. 18, 1999

(86) PCT No.: PCT/EP99/10106

§ 371 (c)(1),
(2), (4) Date: Oct. 1, 2001

(87) PCT Pub. No.: WO00/37108

PCT Pub. Date: Jun. 29, 2000

(30) Foreign Application Priority Data

Dec. 21, 1998 (DE) .......................... 198 59 045

(51) Int. Cl.$^7$ .......................... A61F 13/00; A61F 9/127
(52) U.S. Cl. ................ 424/422; 424/450; 514/937; 514/938
(58) Field of Search ................. 424/400, 450, 424/422; 514/937, 938

(56) References Cited

U.S. PATENT DOCUMENTS

| | | | | |
|---|---|---|---|---|
| 4,678,808 A | * | 7/1987 | Ward et al. | 514/560 |
| 4,869,900 A | | 9/1989 | Pozzi et al. | |
| 4,952,409 A | * | 8/1990 | Bando et al. | 424/450 |
| 5,693,337 A | * | 12/1997 | Suzuki et al. | 424/450 |

FOREIGN PATENT DOCUMENTS

| | | |
|---|---|---|
| WO | WO 97/03651 | 2/1997 |
| WO | WO 99 56776 | 11/1999 |

OTHER PUBLICATIONS

Punz et al (Clinical Nutrition Apr. 1998; 17 (2): 85–87).*
Fuller (AM. J. Cardiology Jan. 1998; 81 (2): 231–3).*
May (Free Radical Bio. Med. 1996; 21 (4): 471–80).*
Steephen et al (Journal Parenteral Enteral Nutrition Nov.–Dec., 1991; 15(6): 647–52).*
Demirbas, A., et al., "Effect of α–Tocopherol on the Prevention of Reperfusion Injury Caused by Free Oxygen Radicals in the Canine Kidney Autotransplantation Model," *Transplantation Proceedings*, vol. 25, No. 3 (Jun. 1993), p. 2274.
Engelhart, K., et al., "Experiments on the parental administration of vitamin E to rats," 16 DGEM–AKE Annual Conference, Stuttgart–Hohenheim, 1997. Aktuelle Ernährungsmedizin, vol. 22, No. 1 (1997), pp. 49–50.
Engelhart, K., et al., "Short–Term Parental Application of α–Tocopherol Leads to Increased Concentration in Plasma and Tissues of the Rat," *Free Rad. Res.*, vol. 29, pp. 421–426.
Ikezawa, T., et al., "Lipid Peroxides in the Mechanism of Ischemia/Reperfusion Injury in Skeletal Muscle—Experimental Studies," *Vascular Surgery*, vol. 27 (1993), pp. 191–201.
Rabl, H., et al., "A Multivitamin Infusin Prevents Lipid Peroxidation and Improves Transplantation Performance," *Kidney International: Official Journal of the International Society of Nephrology*, vol. 43, No. 4 (Apr. 1993), pp. 912–917.
Selliak, S., et al., *Ceylon Medical Journal*, vol. 40 (1995), pp. 97–100.
Search Report of Apr. 20, 2000.

* cited by examiner

Primary Examiner—Thurman K. Page
Assistant Examiner—Sharmila S Gollamudi
(74) Attorney, Agent, or Firm—Katten Muchin Zavis Rosenman; Gilberto M. Villacorta; Serge Sira

(57) ABSTRACT

The invention relates to an oil-in-water emulsion comprising, as an active ingredient, α-tocopherol or the stereoisomers thereof and comprising, as an emulsifier, phospholipids. The inventive emulsion is used in order to attain a protective action against damages to human organs resulting from peroxidation. The emulsion contains a α-tocopherol content, with regard to action, of 1.48 g/l to 30 g/l RRR-g(a)-tocopherol, 0–25 g/l of an oil which is compatible with I.V. administration, and 0.25 g/l to 3 g/l of a phospholipid. The emulsion is preferably administered as an infusion and is especially used to reduce damages resulting from peroxidation due to ischemia and /or reperfusion and, among other things, during an organ transplantation.

10 Claims, No Drawings

OIL-IN-WATER EMULSION FOR PROTECTING HUMAN ORGANS AGAINST PEROXIDATION

This application is a 371 of PCT/EP/99/10106 filed Dec. 18, 1999.

DESCRIPTION

The invention relates to an oil-in-water emulsion exhibiting a protective action against damages to human organs resulting from peroxidation, containing α-tocopherol, the main component of vitamin E, as an active ingredient whose content considerably exceeds that of vitamin E, as usually contained in multi-vitamin solutions. This emulsion is especially directed against peroxidation which occurs when organs are exposed to a deficient blood supply, or even a complete cessation of the blood supply, followed by a renewed complete blood supply. This condition can occur with any type of closure of a blood vessel serving to supply an organ, with the renewed blood supply mostly being restored by surgical intervention. However, it is also deliberately produced in the course of operations on organs, such as the kidneys, liver, intestines or heart, by clamping the blood vessel carrying the blood supply in order to be able to carry out a surgical intervention on the organ. Once the operation is finished, the blood supply is then restored. This solution can likewise be used successfully during the course of an organ transplantation. As a rule this emulsion is applied exclusively intravenously, especially as an infusion. However it is also suitable for use as an additive to organ preservation solutions in the course of organ transplantations.

Vitamin E is an essential, fat-soluble vitamin that can effectively combat peroxyl radicals of lipids even in relatively low concentrations. It is moreover highly effective in the protection of cell membranes against peroxidation, it being also assumed in this case, that this effectiveness is also based on protection against lipid oxidation, i.e. double bonds of lipids present in the cell membrane are protected against destruction by peroxidation, the cell membrane remaining intact in its structure and strength. α-Tocopherol is the main component of vitamin E. The term vitamin E also covers the other tocopherols such as β, γ, and δ-tocopherols, and further tocol and tocotrienol derivatives. The α-tocopherol has the formula 2, 5, 7, 8 tetramethyl-2- (4',8',12'-trimethyltridecyl) chroman-6-ol, it has 3 chiral centres in the positions 2, 4' and 8', and there are therefore 8 stereoisomeric forms (RRR, SSS, RRS, SSR, RSR, SRS, RSS and SRR). Only the RRR form occurs in nature, and this is also the most strongly effective. In addition there are the other stereoisomers which can be obtained synthetically, like the racemate form, all-rac-α-tocopherol, which is a mixture of equal proportions of all 8 stereoisomers. It is usual to relate the effectiveness of all the stereoisomeric forms, as well as that of the all-rac form to the effectiveness of the RRR form. Thus for example, the effectiveness of 1 g of the all-rac-α-tocopherol corresponds to that of 0.74 g of the RRR-stereoisomer, and that of 1 g of the SRR-stereoisomer to that of 0.31 g RRR-α-tocopherol. The anti-oxidant effect is ascribed to the phenolic OH group on the chroman ring.

It is usual to administer vitamin E perorally in multi-vitamin preparations; vitamin E is also frequently contained in the form of esters of the a-tocopherol in multi-vitamin solutions which can be administered parenterally or also intravenously, so that any vitamin E deficiency can be eliminated or prevented.

WO 97/03651 has also already described oil-in-water emulsions with a content of vitamin E in the oil phase, in which the vitamin E is the only vitamin present, but does not represent the active ingredient of the oil-in-water emulsion. Active ingredients are rather substances of low solubility such as, preferably, itraconazole, an antimycotic or the anti-cancer drug Taxol, and/or its derivatives, whose solubility in the lipid phase is understood to be improved by the addition of vitamin E, especially α-tocopherols. The aim is to achieve the greatest possible vitamin E content in the lipid phase, also including emulsions containing vitamin E as the only component of the lipid phase. These requirements are primarily fulfilled by the choice of synthetic emulsifiers of the copolymer class (poloxamers and/or pluronic types). In this case, with a 10 and 20% lipids content in the emulsion, these lipids consisting of a mixture of soya oil and vitamin E in the weight ratio of 1:1, with a content of poloxamer 407/pluronic 127 in a quantity of 2 and/or 4% stable emulsions, which, especially in the case of an emulsifier content of 4% satisfy the solubility for Taxol. These synthetic emulsifiers could also be used for the production of oil-free vitamin E emulsions. On the other hand, if phospholipids, especially egg lecithin, are used as emulsifiers, oil-vitamin E ratios of 1:1 are not achieved in an emulsion which is sufficiently stable, and the production of vitamin E as emulsions containing a single lipid substance is not possible according to this publication, see example 7, according to which, when egg lecithin is used as an emulsifier with a vitamin E content of 10 or 50% and egg lecithin contents of 0.4 to 4%, no stable emulsions could be obtained. Examples in which stable emulsions were obtained with phospholipids, have, in all cases when the soya phosphatide epicuron is used, an oil content of 30% and a vitamin E content of 5%, the soya phosphatide content amounting to 4%.

The only example in which egg lecithin was used as an emulsifier is example 4, where, converted to 1000 ml, the soya oil content in the emulsion amounted to 330 ml, that of vitamin E amounted to 80 g and that of egg lecithin 66 g. The i.v. administration of such emulsions to susceptible patients is not possible.

A special problem is damage resulting from peroxidation occurring in the case of ischaemia and subsequent reperfusion, because these generally concern the most seriously ill patients, e.g. those undergoing serious operations on the liver, heart or kidneys, or even organ transplantations. The opinion has arisen that this damage can be mitigated by the administration of vitamin E, if it can be ascribed to lipidperoxidation. Animal experiments have therefore been carried out, e.g. on mice or rats, to see whether this damage can in fact be combated by vitamin E. In many cases, but not always, these experiments showed that peroxidation damage resulting from ischaemia and/or perfusion can be reduced by the administration of vitamin E/α-tocopherol.

Amongst several application possibilities, such as oral or intraperitoneal administration to the experimental animals, intravenous application to experimental animals was also examined. Thus, for example, Ikezawa T., Nishikimi N. and Oba Y., in their work "Lipidperoxides in the mechanism of ischemia/reperfusion injury in skeletal muscle; experimental studies" VASC SURG 1993, 27, 191–201 established that on an ischaemia-reperfusion model, on skeletal muscles of dogs, the administration of 500 mg vitamin E (all-rac-tocopherolacetate, preparation with polyethylene glycol 400), given for a few minutes directly before reperfusion, the ischaemia-reperfusion damage to be expected was reduced. This was also manifested by the fact that the significant increase in serum creatine-phosphokinase, which is regarded as a sign of rhabdomylisis occurring, is suppressed during the reperfusion phase by the administration of α-tocopherol, and also by the fact that the increase in lipid peroxides in the serum, measured as a coloured reaction product (TBARS, thiobarbituric acid reactive substances) of the reaction of the malonodialdehyde (MDA) produced with thiobarbituric acid, was prevented by this administration. Furthermore, in the case of rats which were given the vitamin E orally via a tube, and intravenously via a central vein catheter in each case for 3 days in doses of 1.0 mg/day orally or 0.5 mg/day intravenously, and were then exposed to oxidative stress, it was shown that by means of intravenous administration, a significant concentration of vitamin E in the plasma and aortic endothelium could be achieved, in comparison with control animals which received no vitamin E, the vitamin E concentration in the plasma also being significantly higher than in the case of those animals which received double the dose of vitamin E orally. This administration of vitamin E showed clear effects with regard to the degree of lipidperoxidation. In the animals which received the vitamin E intravenously, the concentration of TBARS in the plasma was significantly lower than in the plasma of the control animals, and also showed no further increase under oxidative stress (Engelhart K., Fuerst P., Biesalski H K, Experiments on the parenteral administration of Vitamin E to rats (abstract) 16 DGEM-AKE annual conference, Stuttgart-Hohenheim, 1997. Aktuelle Ernahrungsmedizin 1997, 22 (1), 49, 50.

Closer details of the α-tocopherol preparation used for such experiments can be found in the work by the same authors, K. Engelhart et al. Free Rad. Res., Vol. 29, pp 421–426, 1998, according to which a commercial fat emulsion was used for the parenteral administration of the α-tocopherol preparation to the rats used as experimental animals, to which was added so much all-rac-α-tocopherol that a concentration of tocopherol in the emulsion of 12.5 mmol/l (=5.4 g/l) was achieved. The commercial fat emulsion contained, per 100 ml, 10 g soya oil, 1.2 g egg lecithin, 2.5 g glycerine, 30 mg oleic acid 3 mg NaOH and 4 μmol/l vitamin E. It thus has, per liter, a content of 100 g soya oil, 12 g egg lecithin, 25 g glycerin, 300 mg oleic acid, and 30 mg caustic soda. Before intravenous administration to the rats used as experimental animals, this emulsion was diluted with sodium chloride solution to the extent that an all-rac-α-tocopherol concentration of 0.58 mmol/l, i.e. 0.025 g/l, resulted. As already described in the aforementioned publication of K. Engelhart, P. Ftirstund and H. K. Biesalski, it was administered to the rats via a central vein catheter for 3 days, in doses of 0.5 mg an all-rac-α-tocopherol/day in each case. As a result, the work of Engelhart et al. in Free Rad. Research, Vol. 29 with regard to the effect of tocopherol application, only described a significant increase in the α-tocopherol level in the cell-associated aortic endothelium.

Finally, the addition of vitamin E to organ preservation solutions in animal experimentation was also examined. (A. Demirbas et al., Transplantation Proceedings 25 (3), (1993), 2274, and Silka Selliak et al., Ceylon Medical Journal 1995, 40, 97–100). In both works, the kidneys treated with vitamin E following successful transplantation showed less peroxidation and better kidney function.

In A. Demirbas et al., α-tocopherol was used as vitamin E, but the work does not specify how it was administered. Silka Selliak on the other hand specified his method. He added to the preservation solution "water soluble Vitamin E (Merck)", which is not tocopherol, but a fragment with vitamin E effect (Trolox), in which the hydrophobic part is missing.

The influence of vitamins with antioxidant effect on peroxidation damage within the framework of an organ transplantation was examined by "Rabl H., Khoschsorur G., Colombo T., Petritsch P., Rauchenwald M., Koeltringer P., Tatzber F., Esterbauer H., "A multivitamin infusion prevents lipidperoxidation and improves transplantation performance". Kidney International 1993, 43 (4): 912–917" on patients who had undergone a kidney transplantation. This was based on the opinion which was still described as a hypothesis at the time, that damage caused by ischacmia and reperfusion in the case of kidney transplantations could be connected with lipidperoxidation, and therefore the inhibition of lipidperoxidation by antioxidants should lead to an improvement in the function of the transplanted kidneys. The investigations were carried out on 30 patients. Following transplantation of a kidney, but still in the ischaemic phase, 30 minutes before reperfusion of the kidney, 16 of these patients received an infusion of 20 ml of a multivitamin solution, diluted to give 500 ml solution, which was licensed under the name Omnibionta. With this solution, each patient received 10 mg α-tocopherolacetate and 0.2 mg α-tocopherol. In addition the solution administered also contained vitamin C, vitamin A and 5 B vitamins, to all of which an antioxidant effect is also ascribed. The multivitamin preparation administered was a water-based preparation. It contained, as co-solvent, 300 mg benzyl alcohol, 1000 mg polysorbate 80, 400 mg propylene glycol, 5000 mg glycerine 85%, 720 mg trometamol and water up to a volume of 20 ml. This solution was diluted to 500 ml with physiological sodium chloride solution. The dose of α-tocopherol corresponded only to the recommended daily requirement for vitamin E, whilst vitamin C was administered in 13 times the daily requirement and vitamin A in 6 times the daily requirement. As shown by evaluation of blood samples of the patients based on determination of malonodialdehyde (MDA) in the plasma at the time of administration of the vitamin solution 30 minutes before reperfusion and 1, 2, 3 and 4 hours after reperfusion, it was possible to prevent an increase in MDA values with the vitamin solution, whereas in the control patients a clear increase in the values was registered, especially 1 hour after commencement of reperfusion. Thus proof was provided, that the administration of this vitamin solution had inhibited lipidperoxidation during reperfusion. At the same time, on the basis of creatinine clearance, an improvement in the kidney function of the transplanted kidney was documented in the case of those patients who had received an infusion of the multivitamin solution. The authors ascribe the essential effect to the vitamin C, whose action was explained by a protective effect for vitamin E, the primary antioxidant, against destruction by free radicals, and thus recycling of vitamin E presumably occurred. Rabl et al. also mentioned that Omnibionta was chosen because it was the only preparation licensed in Austria with effective antioxidant vitamins. It was therefore by no means a question of choice. This is also obvious, considering that it was a matter of an aqueous vitamin infusion solution, which required, as a means of dissolving the hydrophobic components, substances such as benzyl alcohol, propylene glycol and other additives which reduce tolerance and cause side effects. Such solutions are scarcely suitable for administration to patients during a serious operation, i.e. when they are in a state of shock. Finally, the tocopherol dose is very low, the main quantity thereof being present as acetate, of which it is known that it has not been fully evaluated. In addition it is to be established that infusion of the preparation only started after the transplantation, 30 minutes before reperfusion, with most of the infusion being given at the start of reperfusion. The success in reducing peroxidation damage was ascertained by the fact that the MDA value 30 minutes before reperfusion, but following transplantation was taken as a base value. However peroxidation damage is to be expected not only during reperfusion, but already occurs during ischaemia, especially if xanthine oxidase, hypoxanthine and xanthine become unphysiologically concentrated in the cells in the ischaemia, as established in animal experiments. Rabl et al. expressly referred to this. The peroxidation damage during reperfusion is mostly ascribable to the concentration of these compounds, which react with the molecular oxygen supplied, with formation of peroxy combinations and radicals. Protection would therefore also be given during the ischaemia phase.

This gave rise to the task of finding a form of α-tocopherol suitable for i.v. application in the form of an infusion, which can be sufficiently tolerated especially by patients in a state of shock. It should make it possible to administer a preferably single dose of tocopherol at a level which will cover the reperfusion as well as the ischaemia phase. This means that it must have a high degree of tolerance.

According to the invention, this is achieved in that α-tocopherol is administered only as such, but not in ester form, the infusion being formulated as an oil-in-water emulsion, which however has a maximum fat content of 2.5% weight/volume, in which phospholipids, especially egg lecithin, serve as emulsifiers, which are also used in a limited quantity, namely a maximum of 0.3%, and contains the RRR-α-tocopherol, all-rac-α-tocopherol or other stereoisomers in a concentration, which, as regards effect, corresponds to that of at least 1.48 g/l RRR-α-tocopherol.

In especially critical cases, the fat content can be dispensed with all together, i.e. the tocopherol represents the only oil component. Fat emulsions with phospholipids, especially with egg lecithin as emulsifier, are known to be well-tolerated, and are superior to synthetic emulsifiers, as they are similar to the chylomicrons. This tolerance, which is already good in itself, is increased still further by the measures according to the invention. With regard to i.v. tolerance, they are therefore clearly superior to systems based on water and organic solvents.

In light of the theory according to WO 97/03651 Danbiosyst UK Ltd, it was not to be expected that stable emulsions with α-tocopherol as an active ingredient and phospholipids as emulsifier could be produced with the low quantities of oil and emulsifier according to the invention, it being particularly surprising that a five-fold increase in the quantity of α-tocopherot per volume unit required no increase in the quantity of oil and emulsifier. With regard to the production of α-tocopherol emulsions without addition of an oil as a carrier component, a prejudice was even created by WO 97/03651, which meant that their successful production was extremely surprising and by no means to be expected.

The object of the invention is consequently an oil-in-water type emulsion with protective effect against peroxidation damage to human organs, especially against damage caused by ischaemia and/or reperfusion, for i.v. administration, containing, relative to the total emulsion, α-tocopherol in the form of all-rac-α-tocopherol, whose stereoisomers and/or mixtures of individual stereoisomers in a quantity corresponding, as regards effect, to that of 1.48 g/l to 30 g/l RRR-α-tocopherol, 0–25 g/l of an i.v. tolerated oil, 0.25 g/l to 3 g/l of a phospholipid as emulsifier, as well as a physiological, non-ionic substance to adjust the osmolarity to physiological values and physiological means for the adjustment of the pH value to 5–9.

As the emulsion according to the invention is preferably administered as an infusion, to patients who are placed under strain due to an existing deficient blood supply, regardless of whether this has been caused by an event, or would have been placed under strain in the course of an operation, and these patients are then placed under further strain by subsequent operations, it is desirable to restrict this strain as much as possible, by the administration of the emulsion according to the invention. In the emulsions according to the invention, an α-tocopherol content corresponding to 3.7 to 22 g/l RRR-α-tocopherol is preferred, and for those emulsions containing an i.v. tolerated oil in addition to α-tocopherol, a quantity of the latter of 1 g/l to 25 g/l is preferred, with the content of the phospholipid used as emulsifier amounting to 1 g/l to 3 g/l. If the addition of oil is dispensed with, a phospholipid content of 0.25 g/l–1.25 g/l is to be preferred with the same α-tocopherol content.

Emulsions without use of an i.v. tolerated oil are especially suitable for administration to patients in a poor or even critical condition. The all-rac-α-tocopherol is preferably used as α-tocopherol.

As oil compenent, all those oils can be used, which are preferably used in fat emulsions to be administered intravenously. These may include in particular sunflower oil, olive oil, corn oil, safflower oil, cotton seed oil and groundnut oil, as well as oils with medium-chained triglycerides, but also various fish oils. Soya oil is especially preferred. As phospholipids, phosphatides of vegetable origin can be used, especially soya phosphatide, but egg phosphatides are preferred. As optimum tolerance of the emulsions according to the invention is aimed at, it is essential to adjust their osmolarity to physiological values. Physiological, non-ionic substances serving this purpose include sugar alcohols, especially mannite and glycerine, but low-molecular amino acids such as glycine can also be used. The use of glycerine is preferred. It may also be advantageous to increase the stability of the emulsion according to the invention by the addition of long-chained fatty acids, the proportion of which relative to the total emulsion should not exceed 0.6%. Oleic acid is especially suitably for this purpose.

Should a further increase in the stability of the emulsion according to the invention be desirable, this can be achieved by further additives which promote stability. These include the following in particular:

Dimyristoylphosphatidyl glycerine, preferably in a quantity of 0.025–0.24 g/l

Ubidecarenon, preferably 0.2 g/l–0.6 g/l

Cholesterin, preferably 0.1 g/l–0.5 g/l

In the above-cited work by Rabl et al., Kidney International 1993, (4), 912–917, an essential part of the peridoxation-inhibiting effect is ascribed to the relatively high proportion of ascorbate in the aqueous-organic solution administered. Vitamin C is a hydrophilic antioxidant. Its inhibiting effect on lipidperoxidation, according to Rabl et al. is based on protection of vitamin E against destruction by free radicals, which amounts to recycling of vitamin E. This is of special significance for the solution used by Rabl et al. as in this, the α-tocopherol content is very small and moreover, most of it is present as acetate. According to the invention, considerably higher vitamin E contents can be used in the emulsion form of the preparation provided, so that no essential effect can be ascribed to a vitamin C content. As ascorbate can have a negative effect on the stability of the emulsion, no absolute ascorbate content was provided. However if there is a deficiency of biologically reducing hydrogen donors (especially vitamin C and glutathione), an ascorbate content can have favourable effects. In such cases, the addition of ascorbate to the emulsion according to the invention in the form of ascorbyl palmitate is prescribed, as this has no essential influence on the stability of the emulsion. It is preferably used in a quantity of 12–25 g/l.

For production of the emulsion according to the invention, the proven method is used, in which the aqueous phase is first produced in the form of a suspension using a rapid agitator, out of water, the emulsifier, the substance used for adjustment of the osmolarity and, if desired, the long-chained fatty acid, this phase being adjusted to the desired pH value of 7–9, by the addition of NaOH. This suspension is then added to the oil phase, either in the form of a mixture of α-tocopherol in the oil or the α-tocopherol alone. Should additional emulsion stabilisers be used, these are added to the aqueous suspension or the oil phase before admixture to the aqueous phase. This mixture is then processed with the same rapid agitator to give a pre-emulsion. If ascorbylpalmitate is to be added to the emulsion according to the invention, this is done after production of the pre-emulsion, preferably after the first homogenisation step.

Equipment such as Becomix or Utraturrax can be used as rapid agitators. Both mixing steps are efficiently carried out at a raised temperature, preferably 60–70° C.

The pre-emulsion of aqueous phase and oil phase thus obtained are then subjected to high-pressure emulsification, possibly using a high-pressure homogeniser or a microfluidiser. The emulsion thus obtained is placed in bottles and heat-sterilised in a rotary autoclave.

The emulsion according to the invention can be used for treatment of all forms of ischaemia with a subsequent reperfusion, regardless of whether this results from an event, or is deliberately produced. The fundamental principle for application according to the invention is that both the whole phase of ischaemia and also reperfusion phase is covered by production of a correspondingly high level of α-tocopherol in the tissue and the administration takes place before any operation on the patient, and sufficiently early for enough time to be available for adjustment of the optimum tissue level. Besides establishing the optimum precondition for effective protection from peroxidation, this also has the advantage that the patient is not yet in the state of shock caused by the operation, which does not apply in the case of administration during the ischaemia phase, 30 minutes before the start of reperfusion as prescribed by Rabl et al.

If it is a question of surgical intervention on a patient, on whom corrective surgery is to be carried out on one of the organs, e.g. partial resection of the liver or an open-heart operation, necessitating cutting off the blood supply to the organ in question, administration of a single dose 12–24 before the start of the operation is prescribed. However, it is also possible to begin with the application as much as 4–5 days before the operation and administer several doses at daily intervals, with the last dose preferably being given no later than 24 hours before the start of the operation. This is recommended so that the optimum tocopherol level in the patient's tissue will in fact have been reached in any case.

If the surgical intervention in question is an organ transplantation, the emulsion according to the invention should if possible be administered to the donor and the recipient, aiming at one application at least 12 hours before the operation in both cases. Should it only be possible to administer the emulsion according to the invention to the donor just before removal of the organ, administration of the emulsion according to the invention to donor and recipient is still indicated, and preferably also addition to the organ preservation solution. This is also recommended, if the organ is to be transported a long distance, and also if it has been possible for the donor to receive the emulsion according to the invention in good time. Addition to the organ preservation solution is especially important, if administration to the donor was not possible.

The doses which are preferably administered amount to 20–50 mg/kg KG, especially 10–40 mg/kg KG α-tocopherolm which are given as an infusion, preferably as a single administration, but also in divided into as many as 4–5 daily doses. These doses also apply to both donor and recipient in the case of an organ transplation, both of whom should receive the full dose.

The protective effect of the emulsion according to the invention was examined on various animal models. In model experiments on rats, the survival rate following partial liver ischaemia and resection was examined. With the model of partial liver resection it was possible to examine "warm" ischaemia. In this, the physiological activity of the organ in question is maintained in spite of ischaemia (insufficient supply of oxygen and nutrients). Any damage caused by ischaemia thus appears very clearly in this model. In contrast to warm ischaemia, in the case of "cold" ischaemia, the physiological activity of the organ in question is reduced and thus ischaemia tolerance is distinctly increased.

Examples of cold ischaemia include animal models for transplantation experiments. Organ damages caused by the ischaemia phase are less distinct with this form of ischaemia and also develop differently over time, due to the changed physiological conditions, as the damages often only become manifest during the course of reperfusion.

Mortality was investigated using the partial liver resection model for 7 days following the operation. According to experience, in this model mortality amounted to 50% following partial liver ischaemia of 60 minutes. With this model, in a surgical intervention, partial liver ischaemia lasting 60 minutes was produced by temporary clamping of the portal vein and arterial branches to the left and middle liver lobes (70% of the whole liver) in these lobes. After this period the blood supply was released again by releasing the clamp (reperfusion). Subsequently the rest of the liver, which had received a normal blood supply in the mean time, was surgically removed (resection). The animals now have only the liver lobes damaged by warm (body temperature) ischaemia.

The application of 40 mg/kg α-tocopherol by means of the emulsion according to the invention immediately before the operation resulted in reduced mortality. This effect was clearly time-dependent. The maximum effect was achieved after application of 40 mg/kg α-tocopherol by means of the emulsion according to the invention 24 hours before the operation. In this test the survival rate amounted to 100%. In a further surgically similar test, the experimental animals were killed 3 hours after the start of the reperfusion phase and the liver damage was examined in liver tissue biopsies and on the basis of liver enzymes.

In these tests, the serum level of the transaminases (GOT, GPT, GIDH and LDH) were measured as markers for the liver damage. As in the case of the survival tests, the protective effect proved to be clearly time-dependent. The maximum effect was achieved when the emulsion according to the invention was applied 24 hours before the operation. Similar results are found in this model in the tissue of the liver biopsies for lipidperoxidation (TBARS).

In the orthotopic liver transplantation model, the transplanted organ is used in spatial correspondence with the replaced organ. With this model for "cold" ischaemia (the donated organ is kept in a cooled solution after removal to preserve the organ for transplantation), in tests on rats the rise in transaminases and the extent of lipidperoxidation following application of the emulsion according to the invention were still more clearly reduced. The reduction in transaminases amounted to approx. 75% on average, the extent of lipidperoxidation, measured on the MDA value, was reduced by more than 50%.

Dose-dependency was measured on the partial liver ischaemia model. The effects described were directly dose-dependent, with relevant reductions in transanimases being observed especially in the range 10–40 mg/kg α-tocopherol.

From these tests the following conclusions can be drawn: by administration of the emulsion according to the invention a limitation of the ischaemia/reperfusion damage to the liver following cold ischaemia and following warm ischaemia can be achieved. In the case of cold ischaemia (transplantation) the enthothelium cells are protected, whilst in the case of warm ischaemia the liver cells are directly protected. Sufficient saturation of the α-tocopherol tissue level is guaranteed by preoperative supplementation by application of the emulsion according to the invention. The organ function is improved on the one hand by the direct protective effect on the liver cells post-operatively, and on the other hand by improved micro-circulation, by protection of the vessel endothelium. Administration of the emulsion according to the invention also has a positive influence on cell damage following ischaemia/reperfusion by a direct antioxidant effect measured on the reduction of lipidperoxidation and by an anti-apoptotic effect in the model of orthotopic liver transplantation.

EXAMPLES

Example 1

25 g anhydrous glycerine were mixed in 220 ml water ad injectionem at a temperature of 60 to 70° C. in a Becomix and mixed with a suspension of 3 g egg lecithin (E-80, company: Lipoid) 0.2 g oleic acid, ca. 0.7 ml 1N caustic soda for adjustment of a pH value of 8 to 9 and 80 ml water. 5.4 g all-rac-α-tocopherol—corresponding to 4 g RRR-α-tocopherol are mixed with 25 g soya bean oil, the mixture is preheated to 60–70° C., added to the aqueous suspension and homogenised at a pressure of 350 bar in a high pressure homogeniser in 4 steps. The emulsion produced is made up to 1000 ml with water ad injectionem, poured into 100 ml glass bottles and heat-sterilised at 121° C. in a rotary autoclave. These 100 ml bottles represent for example a daily dose for application to humans in the case of transplantations, e.g. of liver or kidneys.

Example 2

25 g anhydrous glycerine, 220 ml water ad injectionem, 3 g egg lecithin, 0.2 g oleic acid and ca. 0.7 ml 1N caustic soda, which are heated to 60–70° C., are gradually placed in a rapid agitator (e.g. Ultra Turrax) and processed to a homogenous suspension. 27 g all-rac-α-tocopherol corresponding to 20 g RRR-α-tocopherol are premixed with 25 g soya bean oil and added to the aqueous solution previously placed in the agitating vessel. Using the rapid agitator, a pre-emulsion is prepared from this, and then homogenised in a microfluidiser at 600 bar in 5 steps. After making up to 1000 ml with water ad injectionem, this is placed in 50 ml bottles and sterilised as described in Example 1.

Example 3

25 g anhydrous glycerine, 0.1 g oleic acid and 1.0 g egg lecithin are processed with 300 ml water, which is adjusted to a pH value of 8–9, in a rapid agitator at 60–70° C. 5.4 g all-rac-αtocopherol corresponding to 4 g RRR-α-tocopherol are added directly to this mixture and processed to a pre-emulsion with the rapid agitator. The homogenisation is carried out as described in Example 2.

After making up to 1 l with water ad injectionem, pouring into 100 ml bottles and heat sterilisation as described in Example 1, the emulsion is suitable for the reduction of oxidation damage, especially in susceptible patients.

Example 4

22.5 g anhydrous glycerine, 220 ml water ad injectionem, 2 g egg lecithin, 0.2 g oleic acid, 0.4 g Ubidecarenon and ca. 0.7 ml 1N caustic soda, which are heated to 60–70° C., are gradually placed in a rapid agitator (e.g. Ultra Turrax) and processed to a homogenous suspension. 3 g all-rac-α-tocopherol corresponding to 2.2 g RRR-α-tocopherol are premixed with 12 g soya bean oil and added to the aqueous solution previously placed in the agitating vessel. Using the rapid agitator a pre-emulsion is prepared from this, and then homogenised in a microfluidiser at 600 bar in 5 steps. After making up to 1000 ml with water ad injectionem this is decanted and sterilised as described in Example 1.

Example 5

22.5 g anhydrous glycerine, 220 ml water ad injectionem, 2.5 g egg lecithin, 0.6 g oleic acid, and ca. 0.7 ml 1N caustic soda, which are heated to 60–70° C., are gradually placed in a rapid agitator (e.g. Ultra Turrax) and processed to a homogenous suspension. 10 g all-rac-α-tocopherol corresponding to 7.4 g RRR-α-tocopherol are premixed with 20 g soya bean oil and added to the aqueous solution previously placed in the agitating vessel. Using the rapid agitator, a pre-emulsion is prepared from this, which is then homogenised once in a microfluidiser at 600 bar. 23.4 g ascorbyl palmitate are dissolved in this coarse emulsion and then homogenised 4 more times at 600 bar. The emulsion thus obtained is further processed as described in Example 4.

What is claimed is:

1. Oil-in-water emulsion exhibiting a protective action against damages to human organs resulting from peroxidation, for intravenous administration, containing, relative to the total emulsion, α-tocopherols in the form of all-rac-αtocopherol, its stereoisomers and/or mixtures of individual stereoisomers in a quantity corresponding, with regard to effect, to that of 1.48 g/L to 30 g/L RRR-rac-α-tocopherol, 0 to 25 g/L of an intravenous tolerated oil, 0.25–3 g/L of a phospholipid as emulsifier, and a physiological, non-ionic substance for adjustment of the osmolarity to physiological values and physiological means for adjustment of the pH value to 7–9.

2. Emulsion according to claim 1, containing the α-tocopherol in a quantity corresponding, with regard to effect, to that of 3.7 g/L–22 g/L RRR-α-tocopherol, the oil in a quantity of 1 g/L to 25 g/L and the phospholipid in a quantity of 1–3 g(L.

3. Emulsion according to claim 1, with α-tocopherol as sole lipid component, containing the α-tocopherol in a quantity corresponding, with regard to effect, to that of 3.7 g/L–22 g(L RRR-α-tocopherol and the phospholipid in a quantity of 0.25–1.25 g/L.

4. Emulsion according to claim 1, characterized in that the α-tocopherol is all-rac-α-tocopherol, the oil is soya oil, the phospholipid is egg lecithin and the means for adjustment of the osmolarity is glycerin.

5. Emulsion according to claim 1, characterized in that it contains up to 0.6% weight/volume, relative to the total emulsion of a long-chained fatty acid.

6. Emulsion according to claim 1, characterized in that it additionally contains means to increase the emulsion stability, selected from the group consisting of:

0.025 g/L–0.24 g/L dimyristoylphosphatidyl glycerin;

0.2 g/L–0.6 g/L Ubidecarenon; and 0.1 g/L–0.5 g/L cholesterine.

7. Emulsion according to claim 1, characterized in that it additionally contains 12–25 g/L ascorbyl-palmitate.

8. Method for the production of the emulsion according to claim 1, characterized in that the phospholipid is processed with water which is adjusted to a pH value of 7–9, with the physiological, nonionic substance for adjustment of the osmolarity and, if desired, with the long-chained fatty acid and/or the acscorbic palmitate, to an aqueous suspension, to which is admixed the α-tocopherol as such or in the form of a premixture with the i.v. tolerated oil and with, possibly, means provided to increase the stability of the emulsion, whereupon the resultant mixture is subjected to high-pressure homogenization.

9. Method of reducing peroxidation damage caused by ischaemia and reperfision during an organ transplantation comprising administering the emulsion according to claim 1 to the donor and the recipient.

10. Method of preserving an organ intended for transplantation comprising adding the emulsion according to claim 1 to a preservation solution.

* * * * *